US005451569A

United States Patent [19]

Wong et al.

[11] Patent Number: 5,451,569

[45] Date of Patent: Sep. 19, 1995

[54] PULMONARY DRUG DELIVERY SYSTEM

[75] Inventors: Jeffrey T.-F. Wong, Hong Kong; Michael S.-C. Tam, Shatin, both of Hong Kong

[73] Assignee: Hong Kong University of Science and Technology R & D Corporation Limited, Hong Kong

[21] Appl. No.: 229,600

[22] Filed: Apr. 19, 1994

[51] Int. Cl.[6] ..................... A61K 38/28; A61K 38/11; A61K 45/08

[52] U.S. Cl. ......................................... 514/3; 514/807; 514/975

[58] Field of Search ............................ 514/3, 807, 975

[56] References Cited

U.S. PATENT DOCUMENTS

| | | | |
|---|---|---|---|
| 4,895,719 | 1/1990 | Radhakrishnan et al. | 424/45 |
| 4,944,941 | 7/1990 | Ammann | 424/85.5 |
| 5,006,343 | 4/1991 | Benson et al. | 424/450 |
| 5,207,220 | 5/1993 | Long | 128/207.14 |
| 5,230,884 | 7/1993 | Evans et al. | 424/45 |
| 5,301,664 | 4/1994 | Sievers et al. | 128/200.23 |

OTHER PUBLICATIONS

Yamamoto et al., CA. 120:226732Y of J. Pharm. Pharmacol., 46(1):14–18 (1994).

Yoshida et al., CA. 116:262569B of JP 90–149545 (Jun. 7, 1990).

Okumura et al., Embase Abstract of Int. J. Pharm., 88/1–3, (63–73), 1992.

Sanchez et al., Medline Abstract of Eur. J. Drug Metab. Pharmakotasot, No. 3 120–4 (1991).

Baglioni et al., Medline Abstract of J. Interferon. Res., 10(5):497–504, Oct. 1990.

Stoltz, CA. 108:137901 of EP. 242643 (Oct. 28, 1987).

Salzmon et al., Medline Abstract of N. Engl. J. Med., 312(17):1078–1084 Apr. 25, 1984.

Hirai et al., CA. 86:145958d of Ger. Offen. DE 2620446 (Mar. 3, 1977).

*Primary Examiner*—Shep K. Rose

*Attorney, Agent, or Firm*—Burns, Doane, Swecker & Mathis

[57] ABSTRACT

The present invention provides a method of improving the efficiency of absorption into the bloodstream of drugs delivered through the pulmonary route. The drug is mixed with surfactant, preferably a surfactant naturally produced by the lung. This method is found to enhance the absorption of pharmaceutical compositions, and in particular those comprising protein, eg insulin, or peptides, eg vasopressin.

21 Claims, 4 Drawing Sheets

PULMONARY DRUG DELIVERY SYSTEM

FIELD OF THE INVENTION

This invention relates to pharmaceutical compositions, and in particular to pharmaceutical compositions adapted for pulmonary delivery, and especially to such compositions having enhanced absorption when delivered by the pulmonary route, and which thereby increase the efficiency of the pulmonary drug delivery route.

BACKGROUND OF THE INVENTION

There are a number of known routes for the delivery of drugs into the human or animal body. Notable among these are intravenous injections and oral delivery systems, for example tablets, capsules or orally taken liquids.

Intravenous injections have the advantage that the drug can be delivered directly into the blood stream. This means that the efficiency of this method is very high and there is little if any wastage of the drug. The amount of drug that must be delivered in a particular dose therefore is small compared to other methods of drug delivery. Non-intravenous injections are also a relatively efficient method of drug delivery.

The major disadvantage of injections, intravenous or otherwise, however, is that they are highly inconvenient, especially for example when repeated drug doses must be given to treat chronic conditions. A patient must either return to a medical professional for the injection, or must learn to give injections themselves. Patients suffering from diabetes mellitus for example must learn to give themselves regular daily injections. Apart from the inconvenience and discomfort this causes, there is also the risk of infection if the needle is not clean.

Oral delivery systems, eg tablets and capsules, are far more convenient but not all drugs can be given orally. Some drugs may not be properly absorbed through the stomach wall, others may irritate the stomach causing an unwanted side effect. Other drugs may be degraded by the gastronintestinal tract. For example, protein-based drugs, such as insulin for the treatment of diabetes, cannot be given orally since they would be degraded by proteolytic enzymes and must be given by injection.

Pulmonary drug delivery, for example through nasal sprays or tracheal instillation, offers an alternative mode of delivery to intravenous and oral systems. For example, vasopressin, an anti-diuretic protein used in the treatment of diabetes insipidus, can be given in the form of a nasal spray.

The disadvantage of pulmonary drug delivery, however, is that it is very wasteful and a relatively large amount of the drug is necessary to ensure that the correct dose is received by the patient. U.S. Pat. No. 5,006,343 to Benson et al discloses a method for the pulmonary delivery of pharmaceutically active substances in which liposomes containing pharmaceutically active substances are mixed with an amount of alveolar surfactant protein. A surfactant is a surface active agent that acts to reduce the interfacial tension between water and other liquids or solids, detergents or emulsifiers are typical examples of surfactants. A known natural surfactant is a detergent-like surfactant produced by the lung. This surfactant comprises 90% phospolipids and 10% protein, the major lipid component being dipalmitoylphosphatidylcholine (DPPC). It is an object of the present invention to provide a further development over the teachings of U.S. Pat. No. 5,006,343 and to provide a method of improving the efficiency of pulmonary drug systems whereby they may become more attractive as an alternative to intravenous injection.

SUMMARY OF THE INVENTION

According to the present invention there is provided a pharmaceutical composition for the therapeutic treatment of humans or animals, comprising an effective amount of a pharmaceutically active agent mixed directly with a physiologically acceptable surfactant.

It has been found that mixing the pharmaceutically active agent in solution with a surfactant has been found to significantly increase the absorption of the pharmaceutically active agent via the pulmonary route. While the precise mechanism by which the present invention works is not yet clear, it is considered that since surfactant is constantly being produced in the lung it must also be constantly reabsorbed and recycled (otherwise there would be an unwanted build up of surfactant in the lung), and when the surfactant is mixed with a drug this re-absorption by the lung of the surfactant increases the absorption of the drug itself. Contrary to the teachings of U.S. Pat. No. 5,006,343 it has been found that it is not necessary to encapsulate the pharmaceutically active agent in a liposome but rather the active agent may be mixed directly with the surfactant. Furthermore, whereas in U.S. Pat. No. 5,006,343 the liposome was mixed with a surfactant protein, it has now been found that beneficial results may be obtained by mixing the pharmaceutical agent with surfactant itself including the lipid component. Indeed it is also possible that beneficial results may be obtained by mixing the pharmaceutically active agent with the lipid component of the surfactant alone.

A preferred surfactant is a detergent-like surfactant produced by the lung and which comprises 90% phospolipids and 10% proteins, the major lipid component being dipahnitoylphosphatidylcholine (DPPC). Such a surfactant may be extracted and isolated from bovine or other animal lungs in a known manner and which may or may not contain SP-A, SP-B and SP-C (Surfactant proteins -A, -B, -C). Other surfactants, however, including artificial surfactants, may also be used provided they are physiologically acceptable.

The invention is particularly applicable to the delivery of drugs which cannot be given orally, or which have localised action in the lung. In particular the invention may be applied to the delivery of protein-based drugs such as insulin and trichosanthin, or peptide-based drugs such as vasopressin.

In this specification the term "pharmaceutically active agent" includes not only substances capable of an immediate pharmaceutical effect, but also any acids, salts and bases thereof or other derivatives which are capable of a pharmaceutical effect when absorbed by the body. Similarly the term "surfactant" embraces any deriviatives thereof capable of becoming surfactants upon pulmonary application.

Pharmaceutical compositions according to embodiments of the invention may be delivered to the patient through any of the conventional pulmonary routes, for example via a nasal spray or by means of tracheal instillation, and the compositions may be delivered either with or without a physiologically acceptable non-active carrier.

The present invention also extends to a method for the manufacture of a pharmaceutical composition, comprising the step of mixing directly an effective amount of a pharmaceutically active agent with a physiologically acceptable surfactant.

The present invention further extends to a method for the therapeutic treatment of humans or animals comprising the pulmonary delivery of an effective amount of a pharmaceutically active agent mixed directly with a physiologically acceptable surfactant.

In one form of the invention the present invention provides a method of the therapeutic treatment of diabetes mellitus, comprising the pulmonary delivery of a pharmaceutical composition comprising an effective amount of insulin mixed with a natural lung surfactant.

BRIEF DESCRIPTION OF THE DRAWINGS

Several embodiments of the invention will now be described by way of example and with reference to the accompanying drawings, in which.

EXAMPLE 1

A sufficient number of rats weighing between 350–400 g were selected. In each rat the carotid artery and jugular vein were cannulated for blood sampling and fluid infusion. The trachea was cannulated for drug delivery. Fluids given through the trachea were either in a volume of 100 μl or 200 μl given in two separate doses 30 minutes apart. 40 μl of insulin (at a concentration of 200 units/ml) was mixed with 60 μl of lung surfactant (at a concentration of 40 mg/ml) and was administered by the tracheal route. Insulin without surfactant was administered intravenously to a control sample.

Figure 1A:
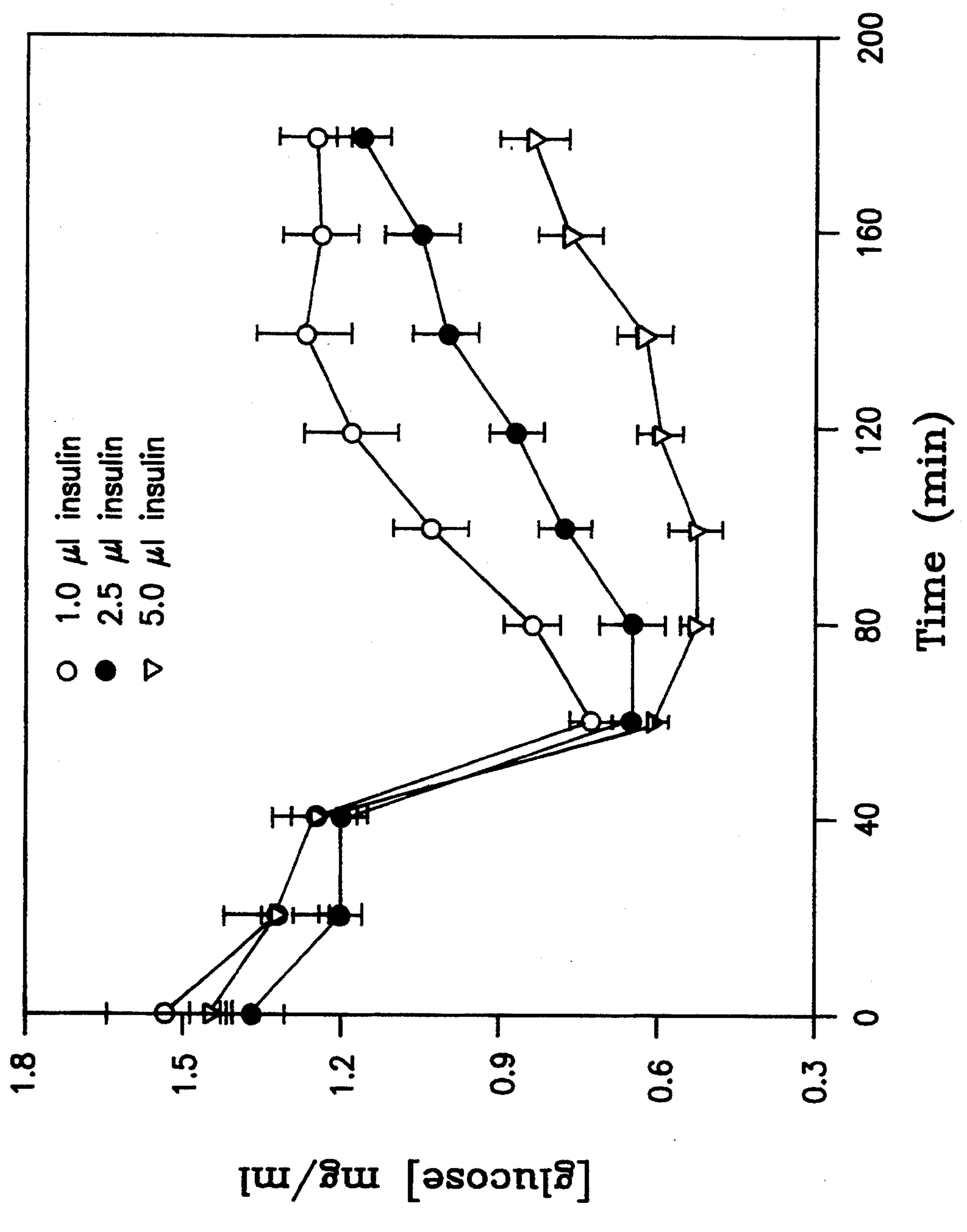
FIGS. 1(*a*) and (*b*) are graphs illustrating the change in plasma concentration after intravenous and tracheal delivery of insulin and illustrating the beneficial effects of the present invention.
Figure 1B:
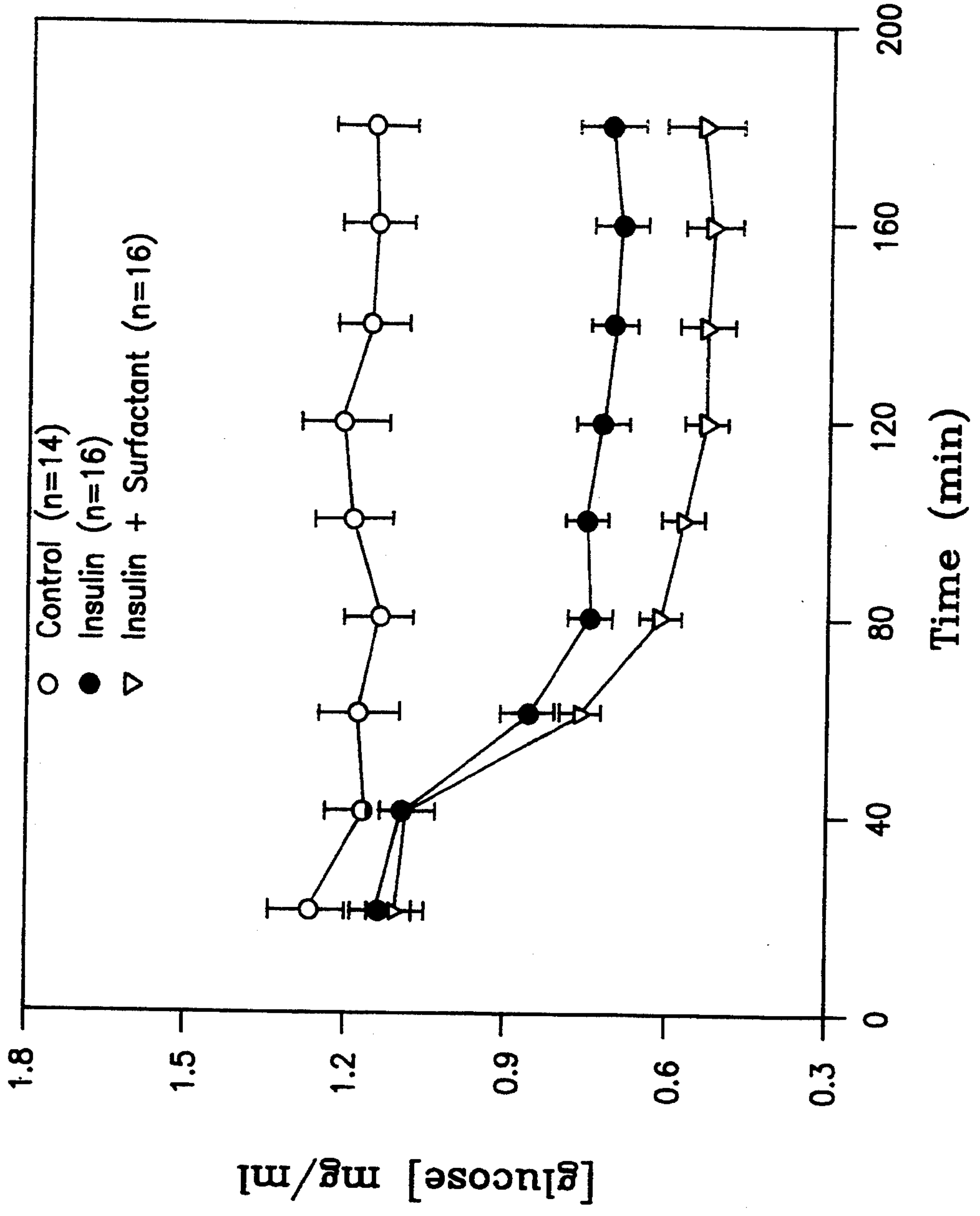

FIG. 1(*a*) illustrates the measured plasma concentration in the blood after intravenous administration of three different amounts of insulin, 1.0 μl, 2.5 μl and 5.0 μl, all at a concentration of 200 units/ml. It will be noted that the plasma concentration falls reaching a minimum after approximately 20 minutes and then starts to climb again, the subsequent increase in concentration being slower following the application of larger amounts of insulin. The data forming FIG. 1(*a*) is of course conventional and is presented here for the benefit of comparison with FIG. 1(*b*).

FIG. 1(*b*) shows the concentration of blood glucose against time for (1) a control sample, (2) a sample receiving tracheal delivery of 40 μl insulin (at a concentration of 200 units/ml) and 60 μl saline, and (3) a sample receiving tracheal delivery of a mixture of 40 μl insulin (concentration of 200 units/ml), and 60 μl surfactant (at a concentration of 40 mg/ml). From the results shown in FIG. 1(*b*) the following conclusions can be drawn: Surfactant increases the hypoglycemic effect of tracheal administered insulin. Without surfactant, tracheal delivery of 8 units of insulin is equivalent to intravenous administration of 0.5 units, it appears therefore that through tracheal administration without surfactant about 6.25% of insulin enters the bloodstream. With surfactant however, tracheal delivery of 8 units of insulin is equivalent to intravenous delivery of 1 unit, about 12.5% of the insulin enters the bloodstream, a two-fold enhancement over tracheal delivery in the absence of surfactant. In addition it will be noted from FIG. 1(*a*) that the hypoglycemic effect of intravenous insulin is relatively short lasting and after approximately 60 mins the glucose concentration begins to rise again. In comparison it will be seen from FIG. 1(*b*) that tracheal delivery of insulin produces longer-lasting effects, there being no significant increase in glucose concentration over a three hour period.

EXAMPLE 2

Tricosanthin (TCS) is a single chain peptide with a molecular weight of 26,000 dalton. Although it has been suggested to have an abortion-inducing effect. its main purpose is an experimental tool.

Figure 2:
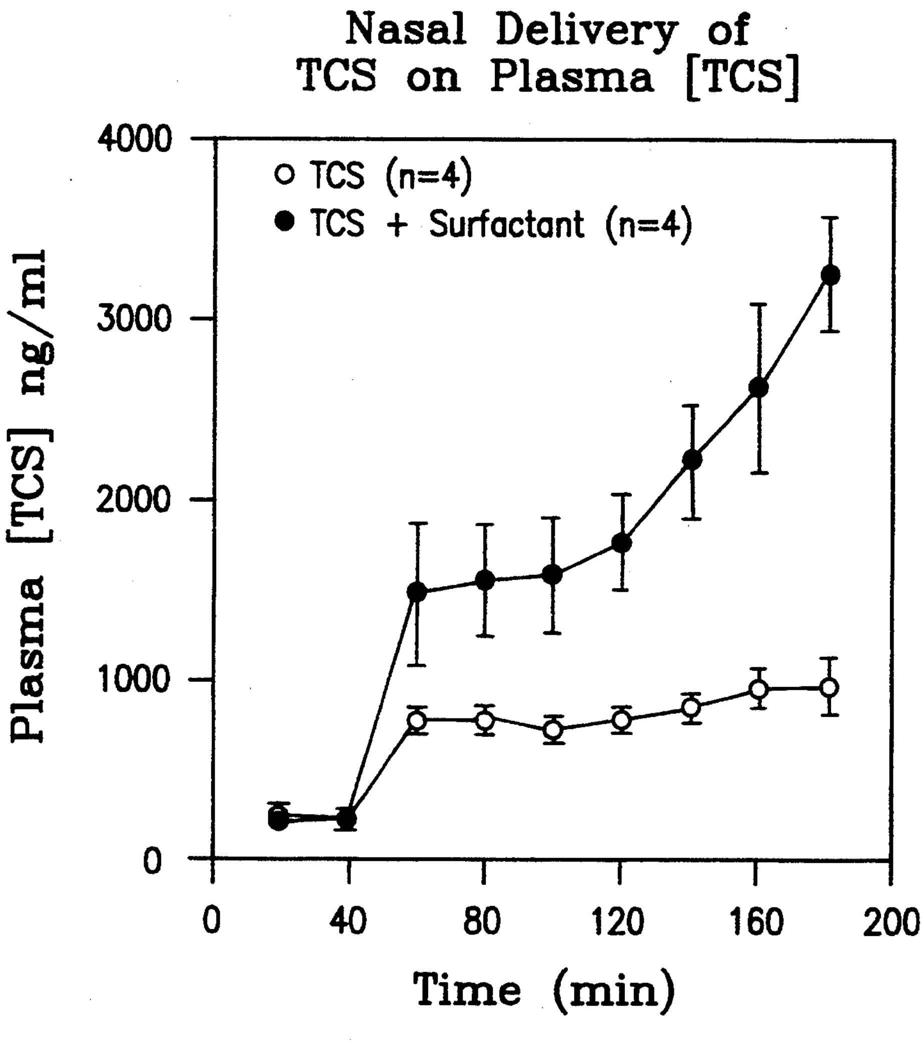
FIG. 2 is a graph illustrating the effect of surfactant on pulmonary trichosanthin absorption, and FIGS. 3(*a*) and (*b*) are graphs illustrating the effect of surfactant on vasopressin absorption when tracheally delivered.

Using the same experimental protocol as in example 1, FIG. 2 shows the measured TCS concentration in the blood after tracheal delivery of (*a*) 100 μl TCS (at a concentration of 25 mg/ml) and 100 μl saline, and (*b*) 100 μl TCS mixed with 60 μl surfactant (at a concentration of 40 mg/ml). The results shown in FIG. 2 show that the addition of surfactant enhances the pulmonary reabsorption of TCS by a factor of approximately 2–3, and furthermore that the degree of enhancement appears to increase with time.

EXAMPLE 3

Figure 3A:
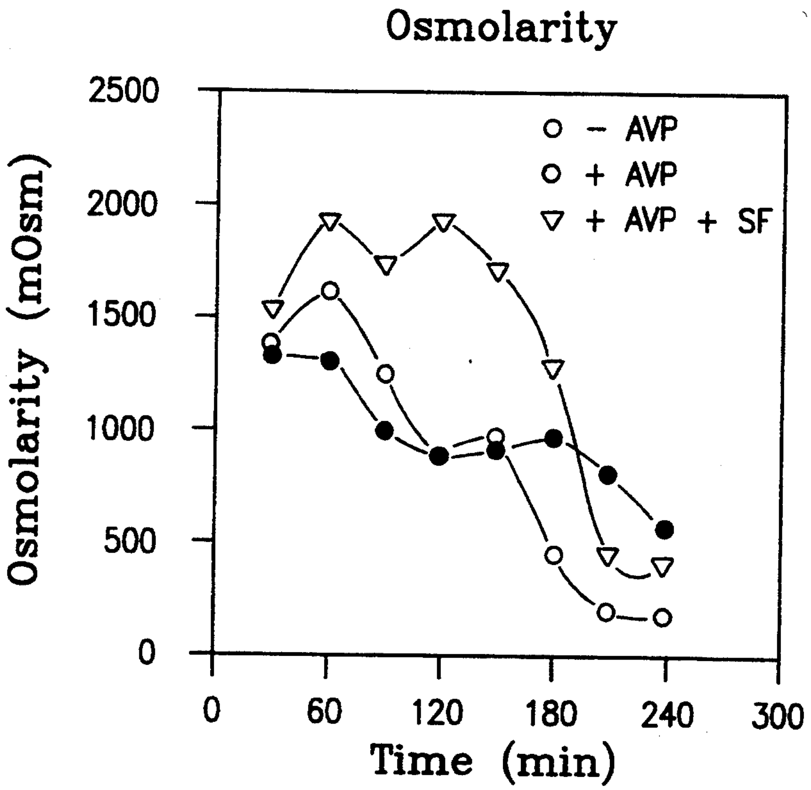
Figure 3B:
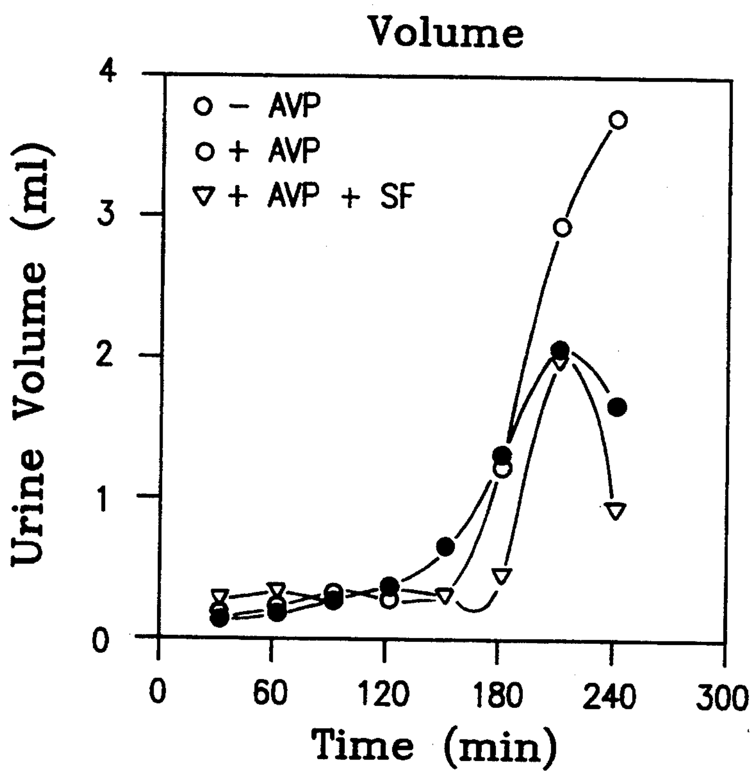

This example illustrates the effect of surfactant on pulmonary vasopressin (AVP) absorption. The experimental details were as follows. 5% glucose was infused at 10 ml/hr throughout the experiment. Urine osmolarity and urine volume resulting from glucose administration alone was contrasted with (1) a delivery of 0.6 units AVP, and (2) delivery of 0.6 units of AVP with 60 μl of surfactant (at a concentration of 40 mg/ml). In (1) and (2) the delivery of AVP and AVP with surfactant was by instillation through the trachea after 30 minutes of glucose infusion which infusion continued. FIGS. 3(*a*) and (*b*) show the results in term of urine osmolarity and volume respectively. Infusion of 5% glucose should have the effect of decreasing urine osmolarity and increasing urine volume. The results show that AVP increases urine osmolarity and reduces urine volume, and that the effect of AVP is enhanced when mixed with surfactant.

We claim:

1. A pharmaceutical composition for the therapeutic systemic non-pulmonary treatment of humans or animals, comprising an effective amount of a pharmaceutically active agent mixed directly with pulmonary surfactant, said pharmaceutically active agent not being encapsulated in a liposome or a reverse micelle.

2. A pharmaceutical composition as claimed in claim 1 wherein said surfactant and is isolated from bovine or other animal lungs.

3. A pharmaceutical composition as claimed in claim 1 wherein said pharmaceutically active agent comprises a protein.

4. A pharmaceutical composition as claimed in claim 3 wherein said pharmaceutically active agent is insulin.

5. A pharmaceutical composition as claimed in claim 3 wherein said pharmaceutically active agent is tricosanthin.

6. A pharmaceutical composition as claimed in claim 1 wherein said pharmaceutically active agent comprises a peptide.

7. A pharmaceutical composition as claimed in claim 6 wherein said peptide is vasopressin.

8. A method for the manufacture of a pharmaceutical composition for the systemic non-pulmonary treatment of humans or animals, comprising mixing directly an effective amount of a pharmaceutically active agent with a pulmonary surfactant, said pharmaceutically active agent not being encapsulated in a liposome or a reverse micelle.

9. A method as claimed in claim 8 wherein said surfactant is isolated from bovine or other animal lungs.

10. A method as claimed in claim 8 wherein said pharmaceutically active agent comprises a protein.

11. A method as claimed in claim 10 wherein said pharmaceutically active agent is insulin or vasopressin.

12. A method as claimed in claim 8 wherein said pharmaceutically active agent comprises a peptide.

13. A method as claimed in claim 12 wherein said pharmaceutically active agent comprises vasopressin.

14. A method for the therapeutic systemic non-pulmonary treatment of humans or animals comprising the pulmonary delivery of an effective amount of a pharmaceutically active agent mixed directly with a pulmonary surfactant, said pharmaceutically active agent not being encapsulated in a liposome or a reverse micelle.

15. A method as claimed in claim 14 wherein the surfactant is isolated from bovine or other animal lungs.

16. A method as claimed in claim 14 wherein said pharmaceutically active agent comprises a protein.

17. A method as claimed in claim 16 wherein said pharmaceutically active agent comprises insulin.

18. A method as claimed in claim 16 wherein said pharmaceutically active agent comprises tricosanthin.

19. A method as claimed in claim 14 wherein said pharmaceutically active agent comprises a peptide.

20. A method as claimed in claim 19 wherein said peptide is vasopressin.

21. A method for the therapeutic treatment of diabetes mellitus comprising the pulmonary delivery of a pharmaceutical composition comprising an effective amount of insulin mixed with natural lung surfactant, said insulin not being encapsulated in a liposome or a reverse micelle.

* * * * *